United States Patent [19]

Jandacek et al.

[11] Patent Number: 4,797,300

[45] Date of Patent: Jan. 10, 1989

[54] COMPOSITIONS CONTAINING NOVEL SOLID, NONDIGESTIBLE, FAT-LIKE COMPOUNDS

[75] Inventors: Ronald J. Jandacek, Cincinnati; James C. Letton, Forest Park, both of Ohio

[73] Assignee: The Proctor & Gamble Company, Cincinnati, Ohio

[21] Appl. No.: 36,836

[22] Filed: Apr. 10, 1987

[51] Int. Cl.$^4$ ............................................. A23D 5/00
[52] U.S. Cl. .................................. 426/549; 426/601; 426/603; 426/611; 426/615; 426/658; 426/804; 536/119
[58] Field of Search ............... 426/607, 601, 611, 804, 426/549, 615, 658, 603; 536/119

[56] References Cited

U.S. PATENT DOCUMENTS

| | | | |
|---|---|---|---|
| 2,999,023 | 9/1961 | Babayan et al. | 426/262 |
| 3,158,490 | 11/1964 | Baur et al. | 426/612 |
| 3,249,600 | 5/1966 | Nobile et al. | 536/119 |
| 3,344,796 | 10/1967 | Yamaji et al. | 131/267 |
| 3,600,186 | 8/1971 | Mattson et al. | 426/611 |
| 4,005,195 | 1/1977 | Jandacek | 424/180 |
| 4,241,054 | 12/1980 | Volpenhein et al. | 424/180 |
| 4,611,055 | 9/1986 | Yamamoto et al. | 536/119 |

FOREIGN PATENT DOCUMENTS

| | | |
|---|---|---|
| 227137 | 9/1985 | German Democratic Rep. . |
| 228457 | 10/1985 | German Democratic Rep. . |
| 52-27694 | 7/1977 | Japan . |
| 53-6220 | 3/1978 | Japan . |
| 53-6219 | 3/1978 | Japan . |
| 58-43744 | 3/1983 | Japan . |
| 58-78531 | 5/1983 | Japan . |
| 58-165737 | 9/1983 | Japan . |
| 49/26220 | 3/1984 | Japan . |
| 59-143550 | 8/1984 | Japan . |
| 59-156242 | 9/1984 | Japan . |
| 61-14123 | 4/1986 | Japan . |

Primary Examiner—Steven Weinstein
Assistant Examiner—Celine Callahan
Attorney, Agent, or Firm—Ronald L. Hemingway; Richard C. Witte

[57] ABSTRACT

Plastic shortening and other food compositions which comprise an edible oil and a fatty acid ester of sucrose wherein the fatty acid groups consist essentially of short chain fatty acid radicals containing from 2 to 10 carbon atoms and long chain fatty acid radicals containing from 20 to 24 carbon atoms in a molar ratio of short chain:-long chain radicals of 5:3 to 3:5, the said esters having a degree of esterification of about 7 to 8. The edible oil can be a triglyceride oil or a nondigestible oil.

14 Claims, No Drawings

COMPOSITIONS CONTAINING NOVEL SOLID, NONDIGESTIBLE, FAT-LIKE COMPOUNDS

FIELD OF THE INVENTION

The invention pertains to plastic shortening and other food compositions which comprise edible oils and novel, nondigestible, solid fat-like compounds which are capable of absorbing large amounts of oil within their crystal structure.

BACKGROUND

Conventional shortening compositions comprise a mixture of triglyceride materials which are respectively, liquids and solids at room temperature. Typically, the liquid triglyceride comprises about 85% of the shortening composition and the solid triglyceride about 15%. The compositions are prepared by hydrogenating a liquid triglyceride to the extent necessary to form the required amount of solid triglyceride within the mixture, or by hydrogenating a fraction of triglyceride to a high degree (Iodine Value from 0 to about 20) to form a high melting solid, and then blending this with a liquid oil to form the solid shortening. In either case, the solid component traps relatively large amounts of the liquid component within its crystal structure, thereby forming a solid shortening, notwithstanding the fact that the amount of solid triglyceride in the shortening composition is relatively small. See U.S. Pat. No. 3,706,578, Bence, issued Dec. 19, 1972.

In recent years considerable attention has been focused on the amount of triglyceride fat in the diet from the standpoint of health concerns about obesity and hypercholesterolemia. Numerous patents have been directed to providing materials which have the physical and gustatory characteristics of triglyceride fats, but which are absorbed to a low extent or not at all by the body. There materials are referred to variously as noncaloric fats, pseudofats, nondigestible fats and fat substitutes. Patents pertaining to such materials include U.S. Pat. Nos. 4,582,927, Fulcher, issued Apr. 15, 1986, (fatty esters of malonic acid); 4,582,714, Volpenhein, issued Apr. 15, 1986, (alpha acetylated triglycerides); and 3,579,548, Whyte, issued May 18, 1981, (triglycerides of alpha-branched chain carboxylic acids.

One particular type of compound which has achieved considerable attention as a nondigestible fat is sucrose polyester (i.e., esterified with a fatty acid). U.S. Pat. Nos. 3,600,186, Mattson, issued Aug. 17, 1971; 4,368,213, Hollenbach et al. issued Jan. 11, 1983; and 4,461,782, Robbins et al. issued July 24, 1984 describe the use of this material as a nondigestible fat in a variety of food compositions.

A problem associated with use of liquid nondigestible fats, i.e., those having a melting point below body temperature (about 37° C.), is an undesired "laxative" effect, which is manifested in leakage of the liquid nondigestible fat through the anal sphincter. U.S. Pat. No. 4,005,195, Jandacek, issued Jan. 25, 1977, discloses the combining of higher melting fatty materials such as solid triglycerides and solid sucrose polyesters with the liquid sucrose polyesters in order to avoid the laxative effect.

An object of the present invention is to provide solid shortening in which the solid fat component is a nondigestible fat material which is highly effective in holding relatively large amounts of oil within its crystal structure.

Another object of the present invention is to provide solid shortening compositions in which both the oil component and the solid component are nondigestible and which do not have the anal leakage problem associated with nondigestible edible oils (i.e., those nondigestible edible oils which have a melting point below body temperature, which is about 37° C.).

Another objective of the present invention is to provide food products which contain nondigestible edible oils but which do not have the anal leakage problem associated with such oils.

For purposes of describing this invention, the term "non-digestible" shall mean being absorbable to an extent of 70% or less (and especially 20% or less) by the human body through its digestive system.

SUMMARY OF THE INVENTION

The invention is directed to edible compositions, especially shortening compositions comprising a liquid edible oil and a nondigestible solid fat material which is a polyester of sucrose wherein the ester groups consist essentially of a mixture of short chain saturated fatty acid radicals ($C_2$–$C_{10}$) and long chain saturated fatty acid radicals ($C_{20}$–$C_{24}$) in a molar ratio of short chain to long chain acid radicals of from about 3:5 to about 5:3, and wherein the degree of esterification is from about 7 to about 8.

DETAILED DESCRIPTION OF THE INVENTION

In accordance with the present invention it has been found that certain sucrose polyesters (SPE's) which are solid at temperatures of about 40° C. and higher, in addition to being suitable nondigestible substitutes for solid fat in the diet, have the ability to bind, within their crystal structure, high levels of edible triglyceride oils and nondigestible oils such as liquid sucrose polyesters, so as to form solid plastic compositions containing a high proportion of oil. Further, this high capacity to bind liquid oils makes these compounds particularly useful in the formulation of food products containing the nondigestible oils, so as to prevent the anal leakage problem associated with the ingestion of such oils.

The novel solid compounds for use in the present invention are polyesters of sucrose wherein the ester groups are a combination of certain short chain and long chain saturated, straight chain fatty acid radicals. The short chain fatty acid radicals contain from 2 to 10 carbon atoms (preferably 6 to 10) and the long chain radicals contain from 20 to 24 (preferably 22) carbon atoms. The molar ratio of short chain to long chain acid radicals in the polyester molecule is from about 3:5 to about 5:3 and the average degree of esterification is from about 7 to about 8, i.e., from about 7 to all 8 of the hydroxyl groups of sucrose are esterified. All proportions and percentages herein are "by weight" unless otherwise specified.

Examples of short chain fatty acid radicals for use in the SPE compounds herein are acetate, butyrate, hexanoate (caproate), octanoate (caprylate) and decanoate (caprate). Examples of suitable long chain fatty acid radicals are eicosanoate (arachidoate), docosanoate (behenate), and tetracosanate (lignocerate). The preferred short chain fatty acid radical is caprylate and the preferred long chain fatty acid radical is behenate. The preferred ratio of short chain fatty acid to long chain fatty acid is 3:5 and it is preferred that all of the hydroxyl groups of sucrose be esterified, i.e., that the compound be the octaester. The most preferred solid SPE compound for use in compositions of the invention is sucrose tricaprylate pentabehenate.

Typically, shortening compositions of the present invention comprise from about 75% to about 90% of a liquid edible oil (i.e., an edible oil which has a complete melting point below about 37° C.) and from about 10% to about 25% of a solid polyester of sucrose wherein the ester groups comprise a mixture of short chain saturated fatty acid radicals ($C_2$–$C_{10}$) and long chain saturated fatty acid radicals ($C_{20}$–$C_{24}$) in a molar ratio of short chain to long chain acids of from about 3:5 to about 5:3, and wherein the degree of esterification is from about 7 to about 8.

Preferably the shortening compositions comprise from about 80% to about 85% of the edible oil and from about 15% to about 20% of the solid SPE.

The compositions herein can be processed into the form of aerated shortening in the conventional manner. This is done by heating the composition to a temperature above the melting point of its solid components to form a melt or liquid fat, rapidly chilling the liquid fat in a scraped surface heat exchanger such as a unit commonly referred to as a "Votator" to produce a cloud of minute crystal nuclei, then passing the composition through a crystallizing unit where crystallization is allowed to continue with mild agitation, and then storing the composition at constant temperature in a final crystallization step known as tempering. The aerating gas is injected into the fat prior to the chilling step and the fat is maintained under high pressure during the chilling and subsequent crystallization stage so that the injected gas is maintained in solution during these steps. After leaving the crystallizing unit the fat is passed through a suitable throttle valve where the pressure is released and the dissolved gas comes out of solution and is dispersed as minute bubbles. The fat is then packed in suitable packages and maintained in a constant temperature room at about 26°–32° C. for 24 to 72 hours ("tempering") to enable the final equilibrium of the stable crystalline phase to be established. Such a process is described by A.E. Bailey, "Industrial Oil and Fat Products," Interscience Publishers, New York, 1951, pages 923–924.

The solid SPE compounds herein can be made according to prior known methods for preparing polyesters of sucrose. One such method is by reacting the acid chlorides of the fatty acids with sucrose. In this method a mixture of the long and short chain acid chlorides can be reacted in one step with sucrose, or the long and short chain acid chlorides can be reacted sequentially with sucrose. Another preparation method is by the process of reacting methyl esters of the fatty acids with sucrose in the presence of a fatty acid soap and a basic catalyst such as potassium carbonate. See, for example, U.S. Pat. Nos. 3,963,699, Rizzi et al., issued June 15, 1976; 4,518,772, Volpenhein, issued May 21, 1985; and 4,517,360, Volpenhein, issued May 14, 1985, all incorporated herein by reference. When using the methyl ester route for preparing the compounds herein, the octaester of the short chain fatty acid is prepared first, then this product is partially interesterified with the methyl ester of the long chain fatty acid in order to obtain the sucrose ester of mixed short chain/long chain fatty acids.

The solid SPE compounds of the present invention are all solids at temperature below about 40°C. They have the ability to trap large amounts of oil within their crystal structure, and as a consequence, can be blended in relatively small amounts (on the order of about 10% to 20%) with liquid oils to convert the oils to solid compositions, i.e., compositions which remain solid at temperatures below about 40°C. The oils can be conventional digestible triglyceride oils such as cottonseed and corn oils, or non-digestible, edible oils.

Some of the solid SPE compounds of the present invention exhibit a beta prime-like crystal structure which is characteristic of triglycerides, however, not all of the solid SPE compounds of the invention exhibit this structure and it is not a required characteristic for the said compounds to be useful in the invention.

Examples of nondigestible edible oils are liquid polyesters of sugars and sugar alcohols (U.S. Pat. No. 4,005,195, Jandacek, issued Jan. 25, 1977); liquid esters of tricarballylic acids (U.S. Pat. No. 4,508,746, Hamm, issued Apr. 2, 1985); liquid diesters of dicarboxylic acids such as malonic and succinic acid (U.S. Pat. No. 4,582,927, Fulcher, issued Apr. 15, 1986); liquid triglycerides of alpha-branched chain carboxylic acids (U.S. Pat. No. 3,579,548, Whyte, issued May 18, 1971); ethers and ether esters containing the neopentyl moiety (U.S. Pat. No. 2,962,419, Minich, issued Nov. 29, 1960); fatty polyethers or polyesters of polyglycerol (U.S. Pat. No. 3,932,532, Hunter et al., issued Jan. 13, 1976); all incorporated herein by reference.

The preferred nondigestible oils are polyol fatty acid polyesters having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms. Examples of these are liquid fatty acid esters of sucrose (e.g., sucrose octaoleate) and liquid fatty acid esters of sorbitol (e.g., sorbitol hexaoleate). Other examples may be found in U.S. Pat. No. 3,600,186, Mattson, issued Aug. 17, 1971, incorporated herein by reference.

The compositions of the present invention (or mixtures of said compositions with other edible materials), are useful in a wide variety of food and beverage products.

For example, they can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, and baked farinaceous snack foods, and other baked salted snacks.

The compositions herein can be used as components of other oleogeneous food products such as margarines, spreads, butter blends, lards, cooking and frying oils, salad oils, popcorn oils, salad dressings, mayonnaise, and other edible oils.

The compositions of the present invention are preferably fortified with vitamins and minerals, particularly the fat-soluble vitamins. The fat-soluble vitamins include vitamin A, vitamin D, vitain E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. Vitamin D is a fat-soluble vitamin well known for use in the treatment and prevention of rickets and other skeletal disorders. "Vitamin D" comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are K1 (phylloquinone), K2 (menaquinone), and K3 (menadione). The amount of the fat-soluble vitamins employed herein to fortify the present low calorie fat materials can vary. If desired, the fat materials can be fortified with a recommended daily allowance (RDA), or increment or multiple of a RDA, of any of the fatsoluble vitamins or combinations thereof. See U.S. Pat. No. 4,005,186, Jandacek et al., issued Jan. 25, 1977, incorporated herein by reference.

Vitamins that are nonsoluble in fat can similarly be included in the present compositions. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present low-calorie fat materials.

Compositions comprising the solid nondigestible sucrose polyesters of the present invention and liquid nondigestible oils (e.g., liquid sucrose polyesters) and particularly useful in combination with particular classes of food and beverage ingredients to formulate low calorie foods. For example, an extra calorie reduction benefit is achieved when the nondigestible fat materials are used with noncaloric or reduced calorie sweeteners alone or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucralose, suosan; miraculin; monollin; sorbitol; xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, metaaminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

Bulking or bodying agents are useful in combination with nondigestible fat materials herein in many food compositions. The buling agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g., lactose.

Similarly, food and beverage compositions can be made that combine nondigestible fat materials with dietary fibers to achieve the combined benefits of each. By "dietary fibers" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and manmade fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

Thes dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Of course, judgment must be exercised to make use of nondigestible fat materials and combinations thereof with other food ingredients. For example, a combination of sweetener and nondigestible fat material would not be used where the specific benefits of the two are not desired. The nondigestible fat materials and nondigestible fat material/ingredient combinations are used where appropriate, and in appropriate amounts.

Many benefits are obtained from the use of nondigestible fat materials in food and beverage compositions, either when used alone or in combination with edible oils and/or other ingredients discussed above. A primary benefit is the calorie reduction achieved when nondigestible fat materials are used as a total or partial fat replacement. This calorie reduction can be increased by using combinations of nondigestible fat materials with reduced calorie sweeteners, bulking agents, or other reduced calorie or nondigestible fats. Another benefit which follows from this use is a decrease in the total amount of fats in the diet. Foods or beverages made with nondigestible fat materials instead of triglyceride fats will also contain less cholesterol, and the ingestion of these foods can lead to reduced serum cholesterol and thus reduced risk of heart disease.

A related benefit is that the use of nondigestible fat materials allows the production of foods and beverages that are stable in terms of shelf stability. Compositions made with the fat materials have acceptable organoleptic properties, particularly taste and texture.

Dietary foods can be made with nondigestible fat materials, to meet special dietary needs, for example, of persons who are obese, diabetic, or hypercholesterolemic. Nondigestible fat materials can be a major part of a low-fat, low-calorie, low-cholesterol diet, and they can be used alone or in combination with drug therapy or other therapy. Combinations of food or beverage products made with nondigestible fat materials can be used as part of a total dietary management regimen, based on one or more of these products, containing nondigestible fat materials alone or in combination with one or more of the above-mentioned ingredients, to provide one or more of the above-mentioned benefits.

When using nondigestible oils in formulating food products comprising fat and nonfat ingredients (e.g., margarines, mayonnaise, baked goods, etc.) in which the fat component comprises a nondigestible oil (e.g., a liquid sucrose polyester such as sucrose octaoleate), the solid SPE's of the present invention can be included in said products to prevent anal leakage of the non-digestible oil which would otherwise occur as a result of ingestion of the products. The solid SPE will generally be used in the food products at a level such that the ratio of the nondigestible oil to solid SPE is from about 9:1 to about 3:1.

This discussion of nondigestible fat material uses, combinations, and benefits is not intended to be limiting or allinclusive. It is contemplated that other similar uses and benefits can be found that will fall within the spirit and scope of this invention.

A listing of representative solid sucrose polyesters for use in compositions of the present invention is shown in the following table.

TABLE 1

Solid Sucrose Polyesters

| | Short Chain Acid* | Long Chain Acid* | Ratio of Short:Long Chain** | Average Degree of Esterification | Melting Point-°C. | Hydroxyl Value |
|---|---|---|---|---|---|---|
| 1 | $C_4$ | $C_{22}$ | 4:4 | 7.99 | 49 | 0.22 |
| 2 | $C_6$ | $C_{22}$ | 4:4 | 7.97 | 44 | 0.65 |
| 3 | $C_8$ | $C_{22}$ | 4:4 | 7.88 | 48 | 3.1 |
| 4 | $C_{10}$ | $C_{22}$ | 4:4 | 7.87 | 47 | 3.2 |
| 5 | $C_8$ | $C_{24}$ | 4:4 | 7.81 | 52 | 5.5 |
| 6 | $C_2$ | $C_{22}$ | 4:4 | 7.87 | 58 | 4.2 |

*Straight chain saturated monocarboxylic acids.
**Ratio of moles of short chain:long chain acid chlorides used in the reaction to prepare the desired products.
Note:
Compounds 1 through 5 have a beta prime-like crystal structure.

The invention will be illustrated by the following examples.

EXAMPLE I

Preparation of Tetrabehenyl Tetracaprylyl Sucrose (Acid Chloride Route)

Chemicals:

| | Mol. Wt. | Wt. (g) | Moles | Mole Ratio |
|---|---|---|---|---|
| A. Reaction | | | | |
| 1. Sucrose | 342.3 | 7 | 0.0204 | 1 |
| 2. Behenyl Chloride (Docosanoyl Chloride) | 358.6 | 30 | 0.0836 | 4.09 |
| 3. Caprylyl Chloride (Octanoly Chloride) | 162 | 15 | 0.0925 | 4.53 |
| B. Solvents | | | | |
| 1. Pyridine | | | | |
| 2. Dimethylformamide | | | | |
| 3. Dichloromethane | | | | |
| 4. Methanol | | | | |

Procedure

Seven grams of sucrose (anhydrous) were dissolved by warming in a mixture of 150 ml pyridine and 75 ml of dimethylformamide (DMF). Both solvents had been dried over 4A molecular sieves.

Thirty grams of the acid chloride of behenic (C22) acid were dissolved in 100 ml of dichloromethane and the acid chloride solution added dropwise to the sucrose solution. The reaction temperature was held at 32° C. by use of a cold water bath. Addition time was 30 minutes.

After addition of the C22 acid chloride, the reaction mixture was warmed to 40° C., removed from the water bath and allowed to stir at ambient temperature for four additional hours.

After four hours of reaction time, 15 grams of caprylyl chloride in 50 ml of dichloromethane were added. Addition time was 30 minutes and the reaction temperature was maintained at 30°-35° C. After addition of the caprylyl chloride, the reaction mixture was allowed to stir overnight.

After stirring overnight, the reaction mixture was diluted with 30 ml of methanol to convert excess acid chlorides to their methyl esters. The reaction mixture was then diluted with 300 ml of dichloromethane and combined in a separatory funnel with 300 ml of a dilute salt (MaCI) solution. The mixture was shaken then allowed to separate.

The organic (dichloromethane) layer was washed a second time with a dilute salt solution followed by washing with dilute HCl (to remove residual pyridine), then with water until the last wash was neutral to pH paper.

The dichloromethane solution was dried over anhydrous sodium sulfate then stripped under vacuum with heating to a liquid residue. The product solidified on standing. The solid product was melted in a hot water bath then extracted three times with methanol (the methanol layers were removed by decantation). The reaction product was stripped again under vacuum and the residue dissolved in 80 ml of dichloromethane. The solution was stirred and 80 ml of methanol were slowly added to induce crystallization. The mixture was again vacuum distilled to displace the dichloromehtane with additional methanol added during distillation. A white precipitate (crystalline) formed and the suspension was cooled in a water bath then filtered to give 40.5 grams of dried product.

Yield - 93% of theoretical.

Analytical

1. Hydroxyl value - 3.1
2. Average degree of esterification - 7.88 (calculated from hydroxyl value as an approximation)
3. Estimated % octaester - 90.6

EXAMPLE II

Preparation of Tetrabehenyl Tetracaprylyl Sucrose (Methyl Ester Route)

An alternative method for preparation of $C_8$–$C_{22}$ sucrose polyesters is by a modification of the process described in U.S. Pat. Nos. 4,518,772, supra, and 4,517,360, supra. Sucrose is reacted with methyl caprylate in the presence of a potassium soap and a basic catalyst such as $K_2CO_3$ to form sucrose octacaprylate. The octacaprylate is then reacted with methyl behenate in the presence of sodium methoxide for an interesterification to the $C_8$–$C_{22}$ product of interest.

Chemicals:

| | Mol. Wt. | Wt. (g) | Moles | Mole Ratio |
|---|---|---|---|---|
| A. Reactions | | | | |
| 1. Sucrose | 342.30 | 300.00 | 0.876 | 1.000 |
| 2. Potassium Behenate | 378.60 | 124.10 | 0.328 | 0.375 |
| 3. Methyl Caprylate | 158.24 | 1663.40 | 10.512 | 12.000 |

-continued

| | | Mol. Wt. | Wt. (g) | Moles | Mole Ratio |
|---|---|---|---|---|---|
| 4. | Methyl Behenate | 354.60 | 2174.40 | 6.132 | 7.000 |
| 5. | Potassium Carbonate | 138.21 | 12.107 | 0.0876 | 0.100 |
| 6. | Sodium Methoxide | 54.00 | (½% by wt. of mixture) | | |
| B. | Solvents | | | | |
| 1. | Methanol | | | | |
| 2. | Hexane | | | | |

Procedure:

Step A - Preparation of Potassium Behenate

Methyl behenate (0.375 moles/mole of sucrose to be used in Step B) is saponified by stirring at reflux in methanol containing an equivalent amount of KOH. The reaction is stirred with heating until all methyl ester has been converted to soap as indicated by infrared analysis. The soap solution is used, as is in the next reaction step.

Step B - Preparation of Sucrose Octacaprylate

Methyl caprylate (12 moles/mole of sucrose) is added directly to the potassium behenate-methyl alcohol solution from Step A above. The mixture is stripped under vacuum to remove the methanol. Sucrose and potassium carbonate are then added to the soap-methyl caprylate mixture and the reaction mixture heated to 135° C. and placed under a partial vacuum.

The reaction is allowed to proceed until the sucrose is converted to its octacaprylate. The endpoint is determined by liquid or super critical fluid chromatography.

The reaction mixture is cooled to 95° C. and 7% $H_2O$ is added to form the hydrate of the soap.

The soap separates as a sludge and is removed by centrifugation, filtration and/or decantation. The oil layer (sucrose octacaprylate/methyl ester layer) is washed several times with hot water, separated and the residual water removed by $N_2$ sparging at 110° C.

The crude octacaprylate is then decolorized with a mixture of filtrol and celite and the bleaching earths removed by vacuum filtration. The excess methyl esters are removed by distillation at 130° C. and 1 mm Hg.

Step C - Preparation of $C_8$–$C_{22}$ Sucrose Polyesters

Sucrose octacaprylate (from Step B above) and 7 moles of methyl behenate are combined with sodium methoxide in a reactor. While stirring, the temperature is raised to 120° C. and the reactor placed under vacuum.

The methyl caprylate formed during interesterification is distilled from the reaction mixture and collected. The reaction is continued until 4–5 moles of methyl caprylate are collected (the ratio of $C_8$–$C_{22}$ on the sucrose may be adjusted by the amount of methyl caprylate removed).

The reaction mixture is then cooled to 90° C. and neutralized with glacial acetic acid.

The product is diluted with hexane and the hexane solution washed several times with hot water.

The water washes are separated and the hexane, along with any residual water, is removed via $N_2$ sparging at 110° C. The product is then rediluted with hexane and is decolorized with a mixture of charcoal and filtrol.

The charcoal/filtrol is removed by vacuum filtration and the solvent removed by vacuum distillation. Excess and/or residual methyl esters are removed by thin film evaporation and the product crystallized from a hexane/methanol solution.

(Steam stripping at 210° C. and 1 mm Hg is an optional final step.)

EXAMPLE III

Preparation of a Reduced Calorie Shortening from a Compound of Example I and a Liquid Triglyceride Six grams of a solid $C_8$–$C_{22}$ sucrose polyester, prepared as in Example I, and 24 grams of Crisco Oil* are weighed into a sample vial. The mixture is heated on a steam bath and mixed by shaking. The mixture is then allowed to cool back to room temperature to form the plastic gel consisting of 20% of the sucrose polyester and 80% triglyceride oil.

*A liquid triglyceride oil marketed by the Proctor & Gamble Company.

The shortening composition can be treated in the conventional manner with air or nitrogen to form an "aerated" shortening.

EXAMPLE IV

Preparation of Nondigestible Shortening from a Compound of Example I and a Liquid Sucrose Polyester Procedure:

Six grams of a solid $C_8$–$C_{22}$ sucrose polyester prepared as in Example I, and 24 grams of a liquid sucrose polyester are combined and heated until all solids are dissolved. The mixture is allowed to cool back to room temperature to form a plastic gel consisting of 20% solid sucrose polyester of Example I and 80% liquid sucrose polyester. The composition is suitable for use as a food fat and does not produce the anal leakage problem which would otherwise result if only the liquid sucrose polyester is used as a food fat.

The shortening composition can be treated in the conventional manner with air or nitrogen to form an "aerated" shortening.

EXAMPLE V

Mayonnaise Composition

A mayonnaise composition of the present invention is made according to the following formula:

| Ingredient | % By Weight |
|---|---|
| Egg Yolk | 8.0 |
| Vinegar | 11.0 |
| Sugar | 2.0 |
| Salt | 1.3 |
| Sucrose octaoleate | 66.0 |
| Tetrabehenyl tetracaprylyl sucrose | 11.7 |
| Total | 100.0 |

EXAMPLE VI

Margarine Composition

A margarine composition of the present invention is made according to the following formula:

| Ingredient | % By Weight |
|---|---|
| Sucrose octaoleate | 68.0 |
| Tetrabehenyl tetracaprylyl sucrose | 12.0 |
| Milk solids | 2.0 |
| Salt | 2.0 |
| Fatty monoglyceride | 15.0 |
| Water | 1.0 |

| Ingredient | % By Weight |
|---|---|
| Total | 100.0 |

What is claimed is:

1. A shortening composition comprising from about 75% to about 90% of an edible oil having a complete melting point below about 37° C. and from about 10% to about 25% of a solid polyester of sucrose wherein the ester groups consist essentially of a mixture of short chain saturated fatty acid radicals containing from 2 to 10 carbon atoms and long chain saturated fatty acid radicals containing from 20 to 24 carbon atoms in a molar ratio of short chain to long chain fatty acid radicals of from about 3:5 to about 4:4, and wherein the degree of esterification is from about 7 to about 8.

2. The composition of claim 1 wherein the edible oil is a triglyceride.

3. The composition of claim 2 wherein the short chain acid radicals of the solid polyester of sucrose contain from 6 to 10 carbon atoms and wherein the long chain acid radical is behenate.

4. The composition of claim 3 wherein the solid polyester of sucrose is tetracaprylyl tetrabehenate.

5. The composition of claim 1 wherein the edible oil is a non-digestible oil.

6. The composition of claim 5 wherein the short chain acid radicals of the solid polyester of sucrose contain from 6 to 10 carbon atoms and wherein the long chain acid radical is behenate.

7. The composition of claims 5 and 6 wherein the nondigestible edible oil is a polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms.

8. The composition of claim 7 wherein the edible oil is a fatty acid polyester of sucrose.

9. The composition of claim 6 wherein the solid polyester of sucrose is tetracaprylyl tetrabehenate.

10. The composition of claim 8 wherein the solid polyester of sucrose is tetracaprylyl tetrabehenate.

11. A food composition comprising nonfat ingredients and fat ingredients, wherein the fat ingredients comprise:
(a) a nondigestible oil having a complete melting point below about 37° C.; and
(b) a solid polyester of sucrose wherein the ester groups consist essentially of a mixture of short chain saturated fatty acid radicals containing from 2 to 10 carbon atoms and long chain saturated fatty acid radicals containing from 20 to 24 carbon atoms in a molar ratio of short chain to long chain fatty acid radicals of from about 3:5 to about 4:4, and wherein the degree of esterification is from about 7 to about 8;

the weight ratio of (a) to (b) being from about 3:1 to 9:1.

12. The composition of claim 11 wherein the short chain acid radicals of the solid polyester of sucrose contain from 6 to 10 carbon atoms and wherein the long chain acid radical is behenate.

13. The composition of claim 12 wherein the nondigestible edible oil is a polyol fatty acid polyester having at least 4 fatty acid ester groups, wherein the polyol is selected from the group consisting of sugars and sugar alcohols containing from 4 to 8 hydroxyl groups and wherein each fatty acid group has from about 8 to about 22 carbon atoms.

14. The composition of claim 13 wherein the nondigestible oil is a fatty acid polyester of sucrose.

* * * * *

UNITED STATES PATENT AND TRADEMARK OFFICE
CERTIFICATE OF CORRECTION

PATENT NO. : 4,797,300

DATED : Jan. 10, 1989

INVENTOR(S) : Ronald J. Jandacek, James C. Letton

It is certified that error appears in the above-identified patent and that said Letters Patent is hereby corrected as shown below:

On the ABSTRACT page, [73] Assignee:
   "Proctor" should read --Procter--

Column 1, line 43, "4,582,714" should read --4,582,715--

Column 1, line 49, after "(i.e.," and before "esterified" add --sucrose in which at least four of the eight hydroxyl groups are--

Column 4, line 68, "C20H29OH" should read --$C_{20}H_{29}OH$--

Column 5, line 20, "fatsoluble" should read --fat-soluble--

Column 5, line 21, "4,005,186" should read --4,005,196--

Column 5, line 34, "and" should read --are--

Column 5, line 60, "buling" should read --bulking--

Column 6, line 18, "Thes" should read --These--

Column 7, line 12, "allinclusive" should read --all-inclusive--

Column 7, line 52, "(Octanoly" should read --(Octanoyl--

UNITED STATES PATENT AND TRADEMARK OFFICE
CERTIFICATE OF CORRECTION

PATENT NO. : 4,797,300

DATED : Jan. 10, 1989

INVENTOR(S) : Ronald J. Jandacek, James C. Letton

It is certified that error appears in the above-identified patent and that said Letters Patent is hereby corrected as shown below:

Column 8, line 35, "dichloromehtane" should read --dichloromethane--

Signed and Sealed this

Sixteenth Day of October, 1990

Attest:

HARRY F. MANBECK, JR.

*Attesting Officer*     *Commissioner of Patents and Trademarks*